United States Patent [19]

Pinter et al.

[11] Patent Number: 5,045,311

[45] Date of Patent: Sep. 3, 1991

[54] PLANT-PROTECTIVE COMPOSITION OF INCREASED STABILITY CONTAINING NONIONIC SURFACTANT ONLY

[75] Inventors: Janos Pinter; Josefne Pal; Eva Kiss, all of Budapest; Erzsebet Shüszler, Erd; Sandor Angyan, Budapest; Laszlo Pap, Budapest; Andras Szegö, Budapest; Tamas Detre, Nagymaros; Tamasne Marmarosi, Biatorbagy, all of Hungary

[73] Assignee: Chinoin Gyogyszer es Vegyeszeti Termekek Gyara Rt., Budapest, Hungary

[21] Appl. No.: 306,025

[22] PCT Filed: Apr. 27, 1988

[86] PCT No.: PCT/HU88/00029

§ 371 Date: May 12, 1989

§ 102(e) Date: May 12, 1989

[87] PCT Pub. No.: WO88/09122

PCT Pub. Date: Dec. 1, 1988

[30] Foreign Application Priority Data

May 18, 1987 [HU] Hungary .............................. 2203/87

[51] Int. Cl.$^5$ ...................... A61K 31/74; A01N 57/00
[52] U.S. Cl. ...................................... 424/78; 514/129; 514/75; 514/103; 514/143
[58] Field of Search ................ 514/129, 103, 143, 75; 424/78

[56] References Cited

U.S. PATENT DOCUMENTS 3,880,997  4/1975  Schmidt et al. ...................... 514/80
4,139,616  2/1978  Ducret et al. ....................... 514/129
4,755,311  7/1988  Burjes et al. ........................ 558/72

FOREIGN PATENT DOCUMENTS 169435  11/1977  Hungary .
40887   3/1987   Hungary .
193990  12/1987  Hungary .
845447  8/1960   United Kingdom ................ 544/337
2050170A 1/1981  United Kingdom .

OTHER PUBLICATIONS

Chem. Ab. 85,83569w, J. B. Brown et al.
Pioc. Int. Cort. Colloid Sortane Sci, Microemulsions Using Nonionic Emulsifiers, Brown, J. B. et al., p. 507 (1975) which is the underlying reference in Chem. Abstracts 85:83569W Cited by the Examiner as Chem. Abstracts (R).

Primary Examiner—thurman K. Page
Assistant Examiner—Peter F. Kulkosky
Attorney, Agent, or Firm—Herbert Dubno; Jonathan Myers

[57] ABSTRACT

The invention relates to an emulsifiable microemulsion concentrate containing a phophoric acid ester and/or thiophosphoric acid ester as active ingredient. In addition to 20 to 80% by weight of active ingredient, the composition comprises: 7 to 70% by weight of a nonionic surface active agent, preferably a block copolymer with a molecular weight of 1000 to 10000 formed from polyethylene oxide and polypropylene oxide, an alkylphenol polyglycol ether, ethoxylated fatty alcohol or a mixture of nonionic surface active agents; 2 to 50% by weight of water; if desired, 1 to 50% by weight of a co-surfactant, preferably $C_{1-8}$ straight or branched chain and/or cyclic alcohol, $C_{3-8}$ straight or branched chain and/or cyclic ketone, esters of $C_{1-6}$ fatty acids with $C_{1-6}$ alcohols or the mixture thereof; and if desired, 15 to 30% by weight of a water-immiscible organic solvent.

10 Claims, No Drawings

PLANT-PROTECTIVE COMPOSITION OF INCREASED STABILITY CONTAINING NONIONIC SURFACTANT ONLY

FIELD OF THE INVENTION

The invention relates to am emulsifiable microemulsion concentrate containing an ester of phosphoric or thiophosphoric acid or their mixture as active ingredient.

BACKGROUND OF THE INVENTION

The preparation of plant-protective agents poses two kinds of problems:

1) the preparation of an active ingredient possessing the desired biological activity; and 2) the formulation of the active ingredient in a composition providing easy handling for the user.

Among the usual formulations of plant-protective agents, the wettable powders (WP-s) and emulsifiable concentrates (EC-s) are most important and represent nearly 90% of the plant-protective agents available commercially at present. Being liquids, the EC compositions are easier to handle, their portioning can be handled by a simple volumetric measurement and, from the viewpoint of labor-safety it is advantageous that during mixing the release of the health-damaging materials into the air is not a problem (which is practically inevitable in the course of e.g. transferring powders from bags to mixing tanks). In addition, the biological activity of the EC compositions is higher than that of the WP compositions. On the basis of the obvious advantages of EC compositions, it could be expected that these formulations would play a predominant role on the market. Actually however, the number of WP compositions is somewhat higher than that of the EC-s. The reason for this is that an EC composition can be prepared only from an active ingredient which is liquid or, when a solvent can be found in which the active ingredient can be dissolved to give a solution of 10 to 85% concentration (depending on the usual concentrations of the application) without any risk of the interim alteration of the active ingredient. An other drawback of the EC compositions arises from their high solvent content whereby they are inflammable and explosive and the environment is polluted. The drawback of the EC compositions can be diminished by formulating the active ingredient in an emulsifiable microemulsion concentrate.

Microemulsion is a colloidal system which, in a first approach differs from a true emulsion in the dimension of its particles which are smaller by an order of magnitude than those of a true emulsion. According to the general definition, this system contains surface active agents and two immiscible liquids, one of them is usually water, though, in principle, it is also possible to prepare a water-free microemulsion by using an other solvent.

The surfactant may be the mixture of even 6 to 8 tensides and additionally, it may contain alcohols or amines of medium chain length as auxillary surfactants (co-surfactants). A peculiarity of this complicated system lies in its thermodynamical stability: it is formed spontaneously from the appropriate components without the input of an outer energy. The direct reason for this formation is that the interfacial tension between the two phases is very small, it approaches zero and transiently it even becomes negative.

In the outer appearance, a microemulsion is a transparent solution as a consequence of the very small size of the disperse particles. The size of the monodisperse spheres varies between 0.01 and 0.2 $\mu$m. Although this system is transparent, all monochromatic lights such as electron or neutron radiation or X rays are scattered by the system whereby the determination of the particle size is also rendered possible.

Being a peculiar colloidal system, a microemulsion may prominently be used for formulating plant-protective agents on the basis of its above characteristics.

An additional advantage of the microemulsion consists in that it contains a lower amount of organic solvent than an EC composition which is preferably from the viewpoint of both environment protection and the danger of fire and explosion. Microemulsions are preferably used in the cases of ULV applications.

It is characteristic of the known microemulsion EC compositions that, in addition to the active ingredient they contain a combination of nonionic and anionic surface active agents as well as a high amount of a co-surfactant (capillary active substance).

In DE-OS Nos. 3,236,240 and 3,235,612 as well as in U.S. patent specification No. 4,469,675 microemulsion formulations are described which contain mixtures of: an alkylphenol polyglycol ether with calcium dodecylbenzenesulfonate; alkylphenol polyglycol ether with triethanolamine dodecylbenzenesulfonate; or polyoxyethylene-distyrene phenyl ether with calcium dodecylbenzenesulfonate and polyethyleneoxide sorbitol monostearate as combinations of nonionic and anionic surface active agents. Further on, each formulation contains a co-surfactant; most of the examples relate to cyclohexanone. The compositions reported in the above-cited United States patent specification always contain polyvinylalcohol, too.

Since the esters of thiophosphoric acid are decomposed even in weakly alkaline media, the anionic surface active agents commonly used for microemulsion compositions cannot be considered for the formulation thereof. In U.S. patent specification No. 4,304,587 an EC composition is described which contains an organic phosphoric acid ester dissolved in a mineral oil, in petroleum solvents, chlorinated hydrocarbons, alcohols, glycols, ethers, esters, ketones or their mixtures by using an anionic phosphate ester and an alkylphenol polyglycol ether nonionic tenside as emulsifying agent.

In GB-PS NO. 2,071,496 EC compositions are reported which contain organic phosphoric or thiophosphoric acid esters as active ingredient; these compositions contain 1 to 30% by weight of active ingredient as well as 20 to 70% by weight of a nonionic emulsifier and 20 to 60% by weight of a mineral oil or a softening agent. In the examples of this patent specification, nonylphenyl polyglycol ether (EO=10) is used as a nonionic emulsifying agent. When this EC composition is poured onto water, a true emulsion is formed spontaneously.

The problems arising from the formulation of phosphoric and thiophosphoric acid esters are avoided by the solution described in GB-PS No. 2,049,425. No effort is made to prepare an EC composition, but a concentrated aqueous true emulsion is prepared which is stabilized by a polymer (polyvinyl alcohol with a polymerization degree below 1500, tragacantha gum, guar gum, alginates, methyl-cellulose, polyacrylic acid and the like) dissolved in water. The droplets of the emulsion are rather large (1 to 50 μm according to the examples) however, because of the high viscosity of the aqueous medium, no sedimentation or creaming has to be considered during the storage. A drawback of this composition is that it can be stored for only six months instead of the usual two years; furthermore, owing to the high viscosity, the composition is more difficult to dissolve than are the usual EC compositions.

An interesting way of formulating phosphoric and thiophosphoric acid esters is described in GB-PS No. 2,050,170, according to which the EC composition contains 10 to 99.5% of an organic acid or a mixture of organic acids. In this composition, the primary role of the tensides, preferably anionic tensides (polyoxyethylenated sorbitol oleate, alkylphenol polyglycol ether and the like) is to increase the wettability and not to stabilize the emulsion formed.

According to HU-PS No. 169,435, nonionic (alkylaryl polyglycol ether) and anionic (alkylbenzenesulfonate) surface active agents are used in a total amount of 10% together with a suitable co-surfactant (cyclohexanone, dimethylformamide and the like) for formulating O-phenyl-thiono-thiolphosphoric acid esters into an EC composition.

On the basis of the prior art described above it can be stated that no microemulsion composition is known which contains an organic phosphoric or thiophosphoric acid ester as active ingredient; furthermore, the formulations developed for microemulsion compositions cannot be adapted for phosphoric or thiophosphoric esters since these compositions contain basic components in amounts sufficient to start the chemical decomposition of the ester or to rapidly decrease the active ingredient during storage.

OBJECT OF THE INVENTION

The object of the present invention is to develop a stable microemulsion concentrate containing a phosphoric and/or thiophosphoric acid ester in a commonly used amount as active ingredient.

SUMMARY OF THE INVENTION

It has been found that stable microemulsion composition can be prepared from organic phosphoric and thiophosphoric acid esters by using only a nonionic surface active agent. The microemulsion state can be adjusted in the characteristic temperature range by varying the concentration of a suitable nonionic surface active agent, optionally by using a co-surfactant (capillary active substance).

The microemulsion compositions according to the invention characteristically containing: 20 to 80% by weight of an organic phosphoric or thiophosphoric acid ester derivative as active ingredient; 5 to 70% by weight of a nonionic surface active agent (preferably alkylphenol polyglycol ether, ethoxylated fatty alcohol, a block copolymer formed from ethylene oxide and propylene oxide or their mixtures; and 2 to 50% by weight of water. Optionally, the compositions may contain 1 to 50% by weight of a co-surfactant (capillary active substance) as well as other usual additives (agents diminishing the evaporation or improving the spreading or strengthening the adhesion). The co-surfactants preferably used in the compositions according to the invention are $C_{1-6}$ straight and/or branched chain alcohols, $C_{6-8}$ cyclic alcohols, $C_{3-8}$ straight and/or branched chain and/or cyclic ketones, esters of $C_{1-6}$ fatty acids with $C_{1-6}$ alcohols and their mixtures. Optionally, the compositions may contain 15 to 30% by weight of a water-immiscible organic solvent, preferably xylene.

If desired, the compositions according to the invention may contain 1 to 40% by weight of an agent enhancing the efficiency such as piperonyl-butoxide.

The systems according to the invention were qualified as microemulsions when their extinction at a defined temperature and at a wave-length of 450 nm was lower than 0.05 (which means a complete transparency) against a xylene solution containing the same substance in the same concentration. In a number of the cases a negative extinction value was obtained, a fact showing that a microemulsion system may be purer, more "shiny" than the true solution. This is visible to the naked eye at extinction values lower than −0.1.

The compositions according to the invention are illustrated by the following non-limiting Examples.

EXAMPLE 1

|  | Parts |
| --- | --- |
| 0,0-Diethyl 0-(2-quinoxalinyl) thiophosphate | 25 |
| Xylene | 25 |
| Nonylphenol polyglycol ether (EO = 10) | 18 |
| Ethyl acetate | 20 |
| Water | 12 |

This composition shows an extinction of −0.18 at 30° C.; a lower cloud point of 24° C. and an upper cloud point of 50° C.

EXAMPLE 2

|  | Parts |
| --- | --- |
| 0,0-Diethyl 0-(2-quinoxalinyl) thiophosphate | 25 |
| Xylene | 25 |
| Nonylphenol polyglycol ether (EO = 10) | 30 |
| Water | 15 |
| Cyclohexanone | 5 |

This composition shows an extinction of 0.01 at 30° C.; a lower cloud point of 26° C. and an upper cloud point of 48° C.

EXAMPLE 3

|  | Parts |
| --- | --- |
| 0,0-Diethyl 0-(2-quinoxalinyl) thiophosphate | 25 |
| Xylene | 25 |
| Nonylphenol polyglycol ether (EO = 10) | 40 |
| Water | 10 |

This composition shows an extinction of −0.07 at 30° C.; a lower cloud point below −5° C. and an upper cloud point of 54° C.

EXAMPLE 4

|  | Parts |
| --- | --- |
| 0,0-Diethyl 0-(2-quinoxalinyl) thiophosphate | 25 |
| Xylene | 25 |
| Block copolymer formed from polyethylene oxide and polypropylene oxide with a | 30 |

-continued

| | Parts |
|---|---|
| molecular weight of about 1500 | |
| Water | 20 |

This composition shows an extinction of −0.315 at 30° C.; a lower cloud point below −5° C. and an upper cloud point of 53° C.

EXAMPLE 5

| | Parts |
|---|---|
| 0,0-Diethyl 0-(2-quinoxalinyl) thiophosphate | 25 |
| Xylene | 32 |
| Block copolymer formed from polyethylene oxide and polypropylene oxide with a molecular weight of about 1500 | 16 |
| Water | 17 |
| Ethyl acetate | 10 |

This composition shows an extinction of −0.085 at 30° C.; a lower cloud point of 28° C. and an upper cloud point of 58° C.

EXAMPLE 6

| | Parts |
|---|---|
| 0,0-Diethyl 0-(2-quinoxalinyl) thiophosphate | 25 |
| Xylene | 30 |
| Water | 17 |
| Ethanol | 10 |
| Block copolymer formed from polyethylene oxide and polypropylene oxide with a molecular weight of about 1500 | 18 |

This composition shows an extinction of −0.032 at 30° C.; a lower cloud point or 3° C. and an upper cloud point of 53° C.

EXAMPLE 7

| | Parts |
|---|---|
| 0,0-Dilauryl hydrogen phosphate | 20 |
| 0-Lauryl dihydrogen phosphate | 20 |
| Water | 50 |
| Block copolymer formed from polyethylene oxide and polypropylene oxide with a molecular weight of about 1500 | 10 |

The composition shows an extinction of 0.03 at 35° C.; a lower cloud point of 32° C. and an upper cloud point of 75° C.

EXAMPLE 8

| | Parts |
|---|---|
| 0,0-Diethyl 0-(2-quinoxalinyl) thiophosphate | 25 |
| Xylene | 25 |
| Block copolymer formed from polyethylene oxide and polypropylene oxide with a molecular weight of about 1500 | 10 |
| Ethyl acetate | 30 |
| Water | 10 |

This composition shows an extinction of 0.0 at 25° C.; a lower cloud point of 16° C. and an upper cloud point of 55° C.

EXAMPLE 9

| | Parts |
|---|---|
| 0,0-Dioctyl hydrogen phosphate | 40 |
| 0-Octyl dihydrogen phosphate | 40 |
| Water | 15 |
| Nonylphenyol polyglycol ether (EO = 10) | 5 |

This composition shows an extinction of 0.01 at 25° C.; a lower cloud point of 8° C. and an upper cloud point of 32° C.

EXAMPLE 10

| | Parts |
|---|---|
| 0,0-Diethyl 0-(2-quinoxalinyl) thiophosphate | 25 |
| Nonylphenol polyglycol ether | 70 |
| Water | 5 |

This composition shows an extinction of −0.03; a lower cloud point below −5° C. and an upper cloud point of 65° C.

EXAMPLE 11

| | Parts |
|---|---|
| 0,0-Diethyl 0-(2-quinoxalinyl) thiophosphate | 25 |
| Nonylphenol polyglycol ether | 70 |
| Water | 2 |
| Ethanol | 3 |

This composition shows an extinction of −0.135; a lower cloud point below −5° C. and an upper cloud point of 61° C.

EXAMPLE 12

| | Parts |
|---|---|
| 0,0-Diethyl 0-(2-quinoxalinyl) thiophosphate | 25 |
| Block copolymer formed from polyethylene oxide and polypropylene oxide with a molecular weight of about 1500 | 24 |
| Cyclohexanone | 1 |
| Water | 50 |

This composition shows an extinction of 0.02 (separates to two phases without cyclohexanone); the lower cloud point is 28° C., the upper cloud point is 31° C.

EXAMPLE 13

| | Parts |
|---|---|
| 0,0-Diethyl 0-(2-quinoxalinyl) thiophosphate | 25 |
| Oleyl alcohol polyethyleneglycol ether (EO = 15) | 5 |
| Ethyl acetate | 50 |
| Water | 20 |

This composition shows an extinction of −0.06 at 25° C.; a lower cloud point of −1° C. and an upper cloud point of 28° C.

EXAMPLE 14

|  | Parts |
| --- | --- |
| O,O-Dibutyl hydrogen phosphate | 13 |
| O-n-Butyl dihydrogen phosphate | 13 |
| Ethoxylated tristyrylphenol (EO = 20) | 5 |
| Ethyl acetate | 19 |
| Water | 50 |

This composition shows an emulsifier extinction of −0.12 at 25° C.; a lower cloud point of −2° C. and an upper cloud point of 56° C.

What we claim is:

1. A stable, plant-protective microemulsion composition free from anionic surfactants and having an extinction value of less than 0.05 at a temperature of 25° to 35° C., which consists essentially of:
   (a) 20 to 80% by weight of a phosphoric acid ester, a thiophosphoric acid ester, or a mixture thereof as active ingredient;
   (b) 5 to 70% by weight of a nonionic surfactant; and
   (c) 2 to 50% by weight of water, wherein said composition has improved storage stability in comparison to that of a composition containing the same active ingredient but which contains a mixture of an anionic surfactant and the nonionic surfactant.

2. The stable, plant-protective microemulsion composition defined in claim 1 wherein the nonionic surfactant is a block copolymer with a molecular weight of 1000 to 10,000 formed from polyethylene oxide and polypropylene oxide.

3. The stable, plant-protective microemulsion composition defined in claim 1 wherein the nonionic surfactant is an alkylphenol polyglycol ether.

4. The stable, plant-protective microemulsion composition defined in claim 1 wherein the nonionic surfactant is an ethoxylated fatty alcohol.

5. The stable, plant-protective microemulsion composition defined in claim 1 wherein the nonionic surfactant is a mixture of nonionic surfactants.

6. The stable, plant-protective microemulsion composition defined in claim 1 further comprising 1 to 50% by weight of a cosurfactant selected from the group consisting of a $C_1$ to $C_8$ straight chain alcohol, branched chain alcohol, cyclic alcohol, and mixtures thereof, $C_3$ to $C_8$ straight chain ketone, branched chain ketone, cyclic ketone, and mixtures thereof, and an ester of a $C_1$ to $C_6$ fatty acid and a $C_1$ to $C_6$ alcohol, and mixtures thereof.

7. The stable, plant-protective microemulsion composition defined in claim 1 further comprising 15 to 30% by weight of a water-immiscible organic solvent.

8. A stable plant-protective microemulsion composition free from anionic surfactants, having an extinction value of less than 0.05 at a temperature of 25° to 35° C., and having a wide temperature range between its upper cloud point and its lower cloud point, which consists essentially of:
   (a) 25% by weight of O,O-diethyl O-(2-quinoxalinyl) thiophosphate as active ingredient;
   (b) 18 to 70% by weight of nonylphenol polyglycol ether having an ethylene oxide number of 10 as a nonionic surfactant; and
   (c) 10 to 15% by weight of water, wherein said composition has improved storage stability in comparison to that of a composition containing the same active ingredient but which contains a mixture of an anionic surfactant and the nonionic surfactant.

9. A stable plant-protective microemulsion composition free from anionic surfactants, having an extinction value of less than 0.05 at a temperature of 25° to 35° C., and having a wide temperature range between its upper cloud point and its lower cloud point, which consists essentially of:
   (a) 25% by weight of O,O-diethyl O-(2-quinoxalinyl) thiophosphate as active ingredient;
   (b) 10 to 30% by weight of a block copolymer formed from polyethylene oxide and polypropylene oxide with a molecular weight of about 1500;
   (c) 25 to 32% by weight of xylene; and
   (d) 10 to 20% by weight of water, wherein said composition has improved storage stability in comparison to that of a composition containing the same active ingredient but which consists a mixture of an anionic surfactant and the nonionic surfactant.

10. The stable, plant-protective microemulsion composition defined in claim 1 wherein the active ingredient is a thiophosphoric acid ester.

* * * * *